(12) United States Patent
Davis et al.

(10) Patent No.: US 6,372,297 B1
(45) Date of Patent: Apr. 16, 2002

(54) WOOD PRESERVATIVE OXATHIAZINES

(75) Inventors: Robert Allan Davis, Cheshire, CT (US); Alex R. A. Valcke, Wechelderzande (BE); Walter Gerhard Brouwer, Guelph (CA)

(73) Assignees: Uniroyal Chemical Company, Inc., Middlebury, CT (US); Crompton Co./Cie, Elmira (CA)

( * ) Notice: Subject to any disclaimer, the term of this patent is extended or adjusted under 35 U.S.C. 154(b) by 0 days.

(21) Appl. No.: 08/967,856

(22) Filed: Nov. 12, 1997

Related U.S. Application Data

(60) Division of application No. 08/295,117, filed on Aug. 24, 1994, now Pat. No. 5,777,110, which is a continuation-in-part of application No. 08/111,386, filed on Aug. 24, 1993, now abandoned.

(51) Int. Cl.[7] .............................. B05D 7/06; B05D 1/18
(52) U.S. Cl. ........................................... 427/440; 427/4
(58) Field of Search ...................... 514/222.5; 504/155, 504/156, 221, 131, 140, 148, 160; 544/2; 252/399; 427/440, 4

(56) References Cited

U.S. PATENT DOCUMENTS

| | | | | | |
|---|---|---|---|---|---|
| 4,376,513 A | * | 3/1983 | Hagar | ......................... | 239/231 |
| 4,569,690 A | * | 2/1986 | Brouwer et al. | ................ | 71/90 |
| 4,675,044 A | * | 6/1987 | Brouwer et al. | ................ | 71/73 |
| 4,847,002 A | * | 7/1989 | Trumble et al. | ......... | 252/400.5 |
| 5,308,859 A | * | 5/1994 | Metzner et al. | .............. | 514/383 |
| 5,712,275 A | * | 1/1998 | Van Gestel | .............. | 514/222.5 |

* cited by examiner

*Primary Examiner*—Michael Barr
(74) *Attorney, Agent, or Firm*—Daniel Reitenbach

(57) ABSTRACT

The present invention provides certain 3-aryl-5,6-dihydro-1,4,2-oxathiazines and their oxides, useful for the long-term preservation of wood and composite wood materials against wood damaging and wood destroying materials. The present invention also provides compositions containing these 3-aryl-5,6-dihydro-1,4,2-oxathiazines and their oxides, and a suitable vehicle therefor. A method of preserving wood is also disclosed in which a fungicidally or bactericidally effective amount of the present 3-aryl-5,6-dihydro-1,4,2-oxathiazines and their oxides, are applied to the wood substrate to be protected.

1 Claim, No Drawings

WOOD PRESERVATIVE OXATHIAZINES

This is a division of application Ser. No. 08/295,117, filed Aug. 24, 1994, now U.S. Pat. No. 5,777,110 which is a continuation-in-part of application Ser. No. 08/111,386, filed. on Aug. 24, 1993, now abandoned.

BACKGROUND OF THE INVENTION

1. Field of the Invention

The present invention relates to a process for preserving wood and composite wood materials from wood damaging organisms, and compositions useful in such process.

This invention more specifically is directed to a class of 3-aryl-5,6-dihydro-1,4,2-oxathiazines and their oxides which are useful against such wood damaging organisms as bacteria, yeasts, and fungi.

This invention is also directed to novel 3-aryl-5,6-dihydro-1,4,2-oxathiazines and their oxides which are useful against such wood damaging organisms as bacteria, yeasts, and fungi.

2. Description of Related Art

The preservation of wood is a subject of great economic importance. For most purposes, untreated wood is entirely unsatisfactory. It will twist, warp, and crack as it dries; it cannot easily be glued or finished, and it is subject to attack of fungi and/or insects. Properly prepared and preserved wood possesses strength and incompressibility while being flexible.

U.S. Pat. No. 4,569,690 refers to various 3-aryl-5,6-dihydro-1,4,2-oxathiazines and their oxides said to be useful as herbicides, plant fungicides, plant dessicants and defoliants. No mention is made of preserving wood materials from damaging organisms.

Chemical Abstracts 103(1):2144u refers to fungicides containing phenyl-alpha-chloroacetamides said to be effective in industrial environments including paints, metal cutting fluids, and to prevent the growth of cellulose degrading fungus on treated wood.

Chemical Abstracts 102(16):133786g refers to resistance to biological attack in wood treated with epoxides. U.S. Pat. No. 4,562,185 refers to 1-oxo-3-aza-cyclopentane derivatives said to be useful as pesticides, especially systemic insecticides, effective against acarids and nematodes and showing residual activity on wood and clay.

U.S. Pat. No. 4,067,862 refers to a process for modification of polymeric materials with a nitrile sulfide. The modified polymers are said to have uses including decorative or protective coatings for wood.

World Patents Index 67-05105G/00 refers to fungicidal 2-mono substituted amino 1-azacycloalkene-1 compounds, said to have fungicidal activity in both plants and other organic materials including wood.

U.S. Pat. No. 4,977,186 refers to wood preservative and soil treatment compositions containing carbamates.

SUMMARY OF THE INVENTION

This invention relates to a compound of the formula

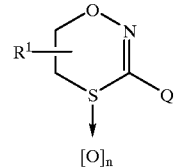

(I)

wherein n is 0, 1 or 2; $R^1$ is hydrogen, $C_1$–$C_4$ linear or branched alkyl, or benzyl; and Q is:

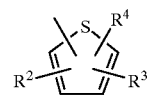

(a)

wherein $R^2$, $R^3$ and $R^4$ are, individually, hydrogen, alkyl, alkoxy, alkylthio, alkoxycarbonyl, halogen, trihalomethyl, cyano, acetyl, formyl, benzoyl, nitro, alkoxyaminomethyl, phenyl, or phenylaminocarbonyl, wherein the alkyl or alkoxy moieties are all $C_1$–$C_4$, linear or branched, with the proviso that at least one of $R^2$, $R^3$ or $R^4$ must be other than hydrogen;

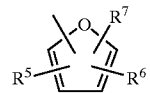

(b)

wherein $R^5$, $R^6$ and $R^7$ are, individually, hydrogen, $C_1$–$C_4$ alkoxy, $C_1$–$C_4$ alkylthio, halogen, trihalomethyl, cyano, acetyl, formyl, benzoyl, nitro, phenyl, or phenylaminocarbonyl, with the proviso that at least one of $R^5$, $R^6$ or $R^7$ must be other than hydrogen;

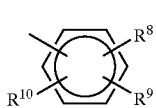

(c)

wherein $R^8$, $R^9$ and $R^{10}$ are, individually, hydroxyl, halo, $C_1$–$C_{12}$ alkyl, $C_5$–$C_6$ cycloalkyl, trihalomethyl, phenyl, $C_1$–$C_5$ alkoxy, $C_1$–$C_5$ alkylthio, tetrahydropyranyloxy, phenoxy, ($C_1$–$C_4$ alkyl)carbonyl, phenylcarbonyl, $C_1$–$C_4$ alkylsulfinyl, $C_1$–$C_4$ alkylsulfonyl, carboxy or its alkali metal salt, ($C_1$–$C_4$ alkoxy)carbonyl, ($C_1$–$C_4$ alkyl) aminocarbonyl, phenylaminocarbonyl, tolylaminocarbonyl, morpholinocarbonyl, amino, nitro, cyano, dioxolanyl, or ($C_1$–$C_4$ alkoxy)iminomethyl; or

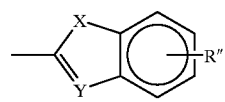

(d)

wherein X is oxygen or sulfur; Y is nitrogen, —CH—, or —C ($C_1$–$C_4$ alkoxy)—; and R" is hydrogen or $C_1$–$C_4$ alkyl.

The compounds of the present invention are useful for the long-term preservation of wood and composite wood materials against wood damaging and wood destroying materials.

The present invention also provides methods useful for the long-term preservation of wood and composite wood materials against wood damaging and wood destroying materials. For the purpose of this invention, a composite wood material is any product made from wood, including, but not limited to, plywood, pressed wood, chipboard, particle-board, wafer board, wood laminated material and the like.

In accordance with the present methods, a wood material is preserved by treatment with a fungicidally or bactericidally effective amount of an active agent represented by the formula below

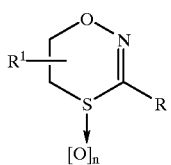

(II)

wherein n is 0, 1 or 2; $R^1$ is hydrogen, $C_1$–$C_4$ linear or branched alkyl, or benzyl; and R is:

(a) phenyl; naphthyl; phenyl substituted with 1–3 of the following substituents:

hydroxyl, halo, $C_1$–$C_{12}$ alkyl, $C_5$–$C_6$ cycloalkyl, trihalomethyl, phenyl, $C_1$–$C_5$ alkoxy, $C_1$–$C_5$ alkylthio, tetrahydropyranyloxy, phenoxy, ($C_1$–$C_4$ alkyl)carbonyl, phenylcarbonyl, $C_1$–$C_4$ alkylsulfinyl, $C_1$–$C_4$ alkylsulfonyl, carboxy or its alkali metal salt, ($C_1$–$C_4$ alkoxy)carbonyl, ($C,$-$C_4$ alkyl)aminocarbonyl, phenylaminocarbonyl, tolylaminocarbonyl, morpholinocarbonyl, amino, nitro, cyano, dioxolanyl, or ($C_1$–$C_4$ alkoxy) iminomethyl;

pyridinyl; thienyl, preferably when n is not 2; furanyl; or thienyl or furanyl substituted with 1 to 3 of the following groups:

alkyl, alkoxy, alkylthio, alkoxycarbonyl, halogen, trihalomethyl, cyano, acetyl, benzoyl, nitro, formyl, alkoxyaminomethyl, phenyl, or phenylaminocarbonyl, wherein the alkyl or alkoxy moiety is $C_1$–$C_4$, linear or branched; or (b)

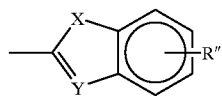

wherein X is oxygen or sulfur; Y is nitrogen, —CH—, or —C ($C_1$–$C_4$ alkoxy)—; and R" is hydrogen or $C_1$–$C_4$ alkyl.

In further accordance with the present invention, there is provided a composition comprising a) a wood preservative amount of a compound of formula I or II, and b) a suitable carrier.

DETAILED DESCRIPTION OF THE INVENTION

A preferred embodiment of the compounds of this invention are those compounds of formula I wherein $R^1$ is hydrogen or $C_1$–$C_4$ alkyl; n is 1 or 2; $R^2$, $R^3$ and $R^4$ are, individually, hydrogen, $C_1$–$C_4$ alkyl, halo, ($C_1$–$C_4$ alkoxy)—carbonyl, or cyano, with the proviso that at least one of $R^2$, $R^3$ and $R^4$ must be other than hydrogen; $R^5$, $R^6$ and $R^7$ are, individually, hydrogen, halo or cyano, with the proviso that at least one of $R^5$, $R^6$ and $R^7$ must be other than hydrogen; $R^8$, $R^9$ and $R^{10}$ are $C_1$–$C_4$ alkyl, $C_1$–$C_4$ alkoxy, nitro, halo, trihalomethyl, or ($C_1$–$C_4$ alkoxy)—carbonyl; X is sulfur; and R" is hydrogen.

More preferred are those compounds of formula I wherein $R^1$ is hydrogen; n is 1 or 2; $R^2$, $R^3$ and $R^4$ are, individually, hydrogen, methyl, ethyl, bromo, chloro, ethyl carboxylate, or cyano, with the proviso that at least one of $R^2$, $R^3$ and $R^4$ must be other than hydrogen; $R^5$, $R^6$ and $R^7$ are, individually, hydrogen, bromo, chloro or cyano, with the proviso that at least one of $R^5$, $R^6$ and $R^7$ must be other than hydrogen; $R^8$, $R^9$ and $R^{10}$ are methyl, ethyl, nitro, fluoro, chloro, or trifluoromethyl.

In a preferred embodiment of the method of the present invention, the compounds of structure II are substituted with $R^1$ being hydrogen, n being one or two, and R has one or 2 of the following values:

phenyl, ($C_1$–$C_6$ alkyl)phenyl, halophenyl, dihalophenyl, biphenyl, ($C_1$–$C_5$ alkyloxy)phenyl, trihalomethylphenyl, nitrophenyl, phenyl substituted with ($C_1$–$C_4$ alkoxy)carbonyl, furanyl, furanyl substituted by ethyl carboxylate, cyano, chlorine, or bromine, thienyl, thienyl substituted with ethyl carboxylate, cyano, chlorine, or bromine, or ($C_1$–$C_6$ alkyl) nitrophenyl.

In a still further preferred embodiment of the method of this invention, $R^1$ is hydrogen, n is one or two, and R is represented by:

4-chlorophenyl, 3-nitrophenyl, 3,4-dichlorophenyl, 3-fluorophenyl, 2-thienyl, 4-methylphenyl, 3-trifluoromethylphenyl, 3-ethanonephenyl, 3,5-dichlorophenyl, 4-trifluoromethylphenyl, 3-methyl-4-nitrophenyl.

In another preferred embodiment of the method of this invention, $R^1$ is hydrogen, and R is

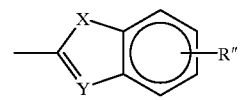

wherein X is sulfur, Y is nitrogen or —CH—, and R" is hydrogen.

The compounds of formula I and II can be prepared utilizing the procedures described in U.S. Pat. No. 4,569,690, the disclosure of which is incorporated herein by reference, or the procedures described in Examples 1–8 below. That patent discloses detailed examples of the synthesis of several 3-aryl-5,6-dihydro-1,4,2-oxathiazines and their oxides by two methods: one utilizing aromatic aldehydes as starting materials and one using arylcarbodithioate esters. Either method is viable and may be understood by one skilled in the art of organic chemical synthesis.

The compositions of this invention include a suitable carrier. Generally, the carrier may be a liquid vehicle for dissolving or suspending the active wood preservative ingredient. The vehicle typically contains at least one of a diluent, an emulsifier, and a wetting agent.

In addition, the carrier may also include other adjuvants conventionally employed in wood preserving compositions, such as organic binding agents, additional fungicides, insecticides, auxilliary solvents, processing additives, fixatives, plasticizers, UV-stabilizers or stability enhancers, water soluble or water insoluble dyes, color pigments, siccatives, corrosion inhibitors, antisettling agents, anti-skinning agents, and the like.

The wood preservative composition is typically supplied as a preparation with the active ingredients dissolved or dispersed in a liquid vehicle or carrier material, such that the active chemical ingredient(s) comprise from about 0.001% by weight up to about 10% by weight of the total composition. More generally, the active fungicidal or bactericidal ingredients will comprise from about 0.1 to 5% by weight, and most often from about 1 to about 5% by weight. For most wood preservative applications, the liquid vehicle can constitute as little as 5% by weight of the preparation. The composition of the present invention can be provided as a ready for use product in the form of aqueous solutions and dispersions, emulsions, aerosol preparations and the like or as a concentrate. The concentrate can be used as is, for example, as an additive for plywood glues, or can be diluted prior to use with additional solvent or suspending agents.

The liquid vehicle is not a critical aspect of the present invention and any liquid that does not interfere with the bactericidal and fungicidal activities of the active ingredients and which is compatible with wood preserving applications potentially can be used in the present invention. Suitable diluents for the liquid vehicle include water and organic solvents including aromatic hydrocarbons such as xylene, toluene, high aromatic petroleum distillates such as solvent naphtha, distilled tar oil and mixtures thereof, alcohols such as butanol, octanol, and glycols, vegetable and mineral oils, ketones such as acetone, petroleum fractions such as mineral spirits and kerosene and the like.

The diluent of the liquid vehicle generally comprises an organic solvent or solvent mixture. The liquid vehicle may contain at least one polar solvent, such as water, in admixture with an oily or oil-like low volatility organic solvent, such as the mixture of aromatic and aliphatic solvents found in white spirits, also commonly called mineral spirits.

Oily or oil-like or organic solvents useful in the present invention preferably have a flash point above 28° C. and a boiling range, at atmospheric pressure, between about 130° C. to 250° C. while low-volatility organic solvents preferably have a flash point above about 55° C. and a boiling range, at atmospheric pressure, between about 180° C. to 3500C. The liquid vehicle is selected to enhance penetration of the active ingredients into the wood or wood product being treated.

An aerosol preparation according to the invention is obtained in the usual manner by incorporating the active ingredients dissolved or suspended in a suitable solvent, in a volatile liquid suitable for use as a propellant, for example, the mixture of chlorine and fluorine derivatives of methane and ethane commercially available under the FREON trademark, or compressed air.

The balance of the composition may include additional ingredients known to be useful in wood preservatives and related products. Such ingredients include organic binding agents, such as alkyd resins; fixatives such as carboxymethylcellulose, polyvinyl alcohol, paraffin and the like; co-solvents, such as ethylglycol acetate and methoxypropyl acetate; and plasticizers such as benzoic acid esters and phthalates, for example, dibutyl phthalate, dioctyl phthalate, and diodecyl phthalate. Optionally, dyes, color pigments, corrosion inhibitors, chemical stabilizers or dryers such as cobalt octate and cobalt naphthenate also may be included depending on specific applications and user preference.

The organic binding agent can be a chemically drying organic binder-forming polymer or a physically drying organic binder forming solids by solvent evaporation. Alkyd resins are a suitable class of organic binding agents; others will be recognized by those skilled in the art. The organic binding agents may themselves be supplied in a liquid vehicle, and in that case the amounts referred to herein for the organic binder are on a solids basis.

As mentioned above, such additional ingredients may include additional fungicides and insecticides. Suitable additional fungicides would be apparent to one skilled in the art, and will vary according to application. Examples include those fungicides known to have wood preservation uses, such as azaconazole, dichlofluanid, acypetacs, propiconazole, imazalil, cyproconazole, hexaconazole, IPBC, isothiozolone, tolylfluanid, chlorotalonil, benzimadazoles, Cu-oxides and Cu-HDO. Suitable insecticides would also be apparent depending upon application, and could include, for example, chlorpyrifos, cypermethrin, fenvalerate, isofenphos, permethrin, silafluofen, deltamethrin, cyfluthrin and imidachloprid. Such additional ingredients are not essential to the practice of the present invention but are included in particular formulations to optimize overall effectiveness and ease of application. The specific examples of suitable constituents for a wood preservative preparation as enumerated above are not meant to be limiting and a wide variety of other possible ingredients will be recognized to one skilled in the art. Similarly, the quantity of such ingredients in any formulation is not critical and can be used in an amount conventionally employed for products designed to be used in wood preserving applications. Normally, the totally formulated compositions may contain from about 0.1% to 95% by weight, and more usually from about 1% to 50% by weight of these additional ingredients on a total solids basis.

The wood preservative composition can be applied by any of the techniques known in the art including brushing, spraying, dipping, and the like. Generally, to obtain an effective treatment, it should be efficient to apply between about 0.05 to 0.4 kilogram of the composition per square meter of wood surface area to be treated, which is equivalent to about 0.01 to 0.08 pound per square foot. An amount of about 0.1 to 0.2 kg/m$^2$, or about 0.02 to 0.04 pound/square foot, is more typical.

The active ingredient may also be applied in the wood by methods known in the art. Such methods include vacuum pressure impregnation, injection and diffusion. Suitable dose ranges for these methods include from about 0.01 to about 6.0 kg/m$^3$ and preferably from about 0.5 to about 6 kg/m$^3$, and more preferably from about 0.5 to about 1.5 kg/m$^3$ of active ingredient in the treated wood.

The composition of the present invention can be prepared by mixing the various ingredients at a temperature at which they are not adversely affected, which usually will be from about $-5°$ C. to 80° C., preferably at a temperature of from about 10° C. to 45° C., and at a pressure of 450 mm Hg to 900 mm Hg, preferably at about 650 mm Hg to 850 mm Hg. Preparation conditions are not critical. Equipment and methods conventionally employed in the manufacture of coating compositions may be advantageously employed.

The following examples are presented for illustrative purposes and are not intended to limiting the scope of this invention in any manner.

The compounds listed in Table 1 were prepared utilizing the procedures described in U.S. Pat. No. 4,569,690. The compounds listed in Tables 2, 3 and 4 were prepared utilizing the procedures described in Examples 1–9 below.

EXAMPLES

Example 1

1.4,2-Oxathiazine,3-(5-chloro-2-thienyl)-5.6-dihydro- (Compound #59)

Methyl 5-chloro-2-thiophenecarbodithioate (61.4g, 0.29 mol) was suspended in methanol (400 ml) with finely powdered hydroxylamine hydrochloride (25g). With stirring, triethylamine (50 ml) in methanol (50 ml) was added dropwise to the suspension, to produce a reaction mixture. During this addition, the reaction mixture was cooled to 5° C. Stirring of the reaction mixture was continued until an orange (from red) color developed in the reaction mixture. Additional triethylamine (100 ml) was then added at once, followed by 1,2-dibromoethane (20 ml). The resultant reaction mixture was then stirred overnight at ambient temperature. The reaction mixture was then refluxed with removal of solvent until a precipitate appeared. The reaction mixture was then cooled and water was added. The reaction mixture was then filtered and the solid collected on the filter was recrystallized from ethanol to produce 3-(5-chloro-2-thienyl)-5,6-dihydro-1,4,2-oxathiazine (mp 74–77° C., 21.4g. Found C 38.5, H 2.94, N 6.45, $C_7H_6ClNOS_2$ requires C 38.27, H 2.73, N 6.38)

Example 2

3-(5-Chloro-2-thienyl)-5,6-dihydro-1.4.2-oxathiazine-4,4-dioxide (Compound #61)

3-(5-Chloro-2-thienyl)-5,6-dihydro-1,4,2-oxathiazine (12g, 0.055 mol) prepared in Example 1, in methylene chlorine (50 ml) and anhydrous magnesium sulphate (10 g) in suspension, was stirred while m-chloroperoxybenzoic acid (34g, 50–60% material) in methylene chloride (250 ml), was added dropwise, to prepare a reaction mixture. The reaction mixture was allowed to warm to 30° C. and after the dropwise addition was externally heated to 35° C. for 10 hours by which time a negative starch/Kl test was obtained. Unwanted m-chlorobenzoic acid was then removed from the reaction mixture by extraction with aqueous sodium bicarbonate. The remaining reaction mixture was washed with water, dried ($MgSO_4$) and evaporated to dryness. The resultant residue was chromatographed on 500 g silica gel eluting with methylene chloride, to produce 3-(5-chloro-2-thienyl)-5,6-dihydro-1,4,2-oxathiazine-4,4-dioxide (mp 113–114° C., 14.3g, Found: C 33.27, H 2.33, N 5.55; $C_7H_6ClNO_3S_2$ requires C 33.40, H 2.39, N 5.57).

Example 3

Synthesis of 3-(5-Chloro-2-thienyl)-5.6-dihydro-1.4.2-oxathiazine-4-oxide (Compound #60)

3-(5-Chloro-2-thienyl)-5,6-dihydro-1,4,2-oxathiazine (12.4g, 0.056 mol) prepared in Example 1, in methylene chloride (50 ml), was stirred while m-chloroperoxybenzoic acid (16.2g) in methylene chloride (250 ml), was added dropwise, to prepare a reaction mixture. The reaction mixture was allowed to warm to 30° C. and after the dropwise addition was externally heated to 35° C. for 10 hours by which time a negative starch/KI test was obtained. Unwanted m-chlorobenzoic acid was then removed from the reaction mixture by extraction with aqueous sodium bicarbonate. The remaining reaction mixture was washed with water, dried ($MgSO_4$) and evaporated to dryness. The resultant residue was chromatographed on 500 g silica gel eluting with methylene chloride, to produce 3-(5-chloro-2-thienyl)-5,6-dihydro-1,4,2-oxathiazone-4-oxide (mp 102° C., 11.4 g, Found: C 35.82, H 2.56, N 5.89, $C_7H_6ClNO_2S_2$ requires C 35.67, H 2.55, N 5.94.

Example 4

Synthesis of 1,4.2-Oxathiazine. 5.6-dihydro-6-methyl-3-(2-thienyl)- (Compound #52)

Methyl-2-thiophenecarbodithioate (47 g, 0.27 mol) in methanol (250 ml) at 0–5° C., was stirred and treated with powdered hydroxylamine hydrochloride (20 g) and followed by dropwise addition of triethylamine (50 ml) in methanol (50 ml) over 2 hours, to prepare a reaction mixture. Additional hydroxylamine hydrochloride (5 g) and triethylamine (10 ml) was added consecutively to the reaction mixture and after 45 minutes, the reaction mixture turned yellow (from red). 1,2-Dibromopropane (26 ml) was then added to the yellow reaction mixture, followed by addition of triethylamine (75 ml). The resultant new reaction mixture was refluxed for 4 hours and then left overnight at ambient temperature. The methanol was removed from the reaction mixture to leave a residue. Water was added to the residue which was then extracted into ethyl acetate, washed with dilute hydrochloric acid (2N, 100 ml), water, and dried ($MgSO_4$). The ethyl acetate was then removed to leave a brown oil which was crystallized with cyclohexane to produce two crops of 5,6-dihydro-6-methyl-3-(2-thienyl)-1,4,2-oxadiazine (11.7 g and 3.7 g, mp 70–72° C.) Found: C 48.90, H 4.66, N 7.17, $C_8H_9NOS_2$ requires C 48.24, H 4.52, N 7.07

Example 5

Synthesis of 5.6-Dihydro-6-methyl-3-(2-thienyl)-1 4.2-oxathiazine-4,4-dioxide (Compound #51)

The 5,6-dihydro-6-methyl-3-(2-thienyl)-1,4,2-oxathiazine produced in Example 4 above (2.8 g, 0.013 mol), was oxidized with m-chloroperoxybenzoic acid (9.8 g) as described in Example 1. Excess peroxide was destroyed with aqueous sodium bisulphite. Extraction produced 5,6-dihydro-6-methyl-3-(2-thienyl)-1,4,2-oxathiazine-4,4, dioxide (from ethanol) (2.1 g, mp 147–148° C.). Found C 42.06, H 3.99, N 6.08, $C_8H_9NO_3S_2$ requires C 41.56, H 3.90, N 6.06.

Example 6

Synthesis of 5.6-Dihydro-6-methyl-3-(2-thienyl)-1.4.2-oxathiazine-4-oxide (Compound #50)

The 5,6-dihydro-6-methyl-3-(2-thienyl)-1,4,2-oxadiazine produced in Example 4 above (2.8 g, 0.013 mol), was oxidized with m-chloroperoxybenzoic acid (3.7 g) as described in Example 1. The resultant product was recrystallized from ethanol to produce 5,6-dihydro-6-methyl-3-(2-thienyl)-1,4,2-oxathiazine-4-oxide (1.3 g, mp 114–115° C.). Found C 44.85, H 4.31, N 6.54, $C_8H_9NO_2S_2$ requires C 44.65, H 4.19, N 6.51.

Example 7

Synthesis of 5.6-Dihydro-3-(2-Benzothiazolyl)-1.4.2-Oxathiazine (Compound #84)

Methyl 2-benzothiazolecarbodithioate (37 g, 0.16 mol) was converted to 1,4,2-oxathiazine using hydroxylamine hydrochloride (13.2 g) and triethylamine (33 ml) as described in Example 4. The ethyl acetate extract of the product was washed successively with diluted hydrochloric acid (2N), water, 5% sodium hydroxide and water. Evaporation of the solvent left a solid residue which was recrystallized from ethanol/ethyl acetate to 5,6-dihydro-3-(2-benzothiazolyl)-1,4,2-oxathiazine (18.0 g, mp 150–151° C.) Found C 50.68, H 3.27, N 11.78, $C_{10}H_8N_2OS_2$ requires C 50.85, H 3.39, N 11.80.

Example 8

Synthesis of 5.6-Dihydro-3-(2-benzothiazolyl)-1.4, 2-oxathiazine-4.4-dioxide (Compound #83)

The 5,6-dihydro-3-(2-benzothiazolyl)-1,4,2-oxathiazine produced in Example 7 (4.2 g, 0.018 mol) was oxidized with m-chloroperoxybenzoic acid as described in Example 5, to produce 5,6-dihydro-3-(2-benzothiazolyl)-1,4,2-oxathiazine 4,4-dioxide (3.7 g, mp 226–227° C.). Found C 44.59, H 3.01, N 10.31, $C_{10}H_8N_2O_3S_2$ requires C 44.78, H 2.99, N 10.45.

Example 9

Synthesis of 5.6-Dihydro-3-(2-benzothiazolyl)-1,4, 2-oxathiazine-4-oxide (Compound #85)

The 5,6-dihydro-3-(2-benzothiazolyl)-1,4,2-oxathiazine produced in Example 7 was oxidized as described in Example 6 to produce 5,6-dihydro-3-(2-benzothiazolyl)-1, 4,2-oxathiazine-4-oxide (2.3 g, mp 192–195° C.). Found C 47.96. H 3.26, N 11.22, $C_{10}H_8N_2O_2S_2$ requires C 47.62, H 3.17, N 11.11.

Tables 1–4 list representative compounds numbered 1–107.

TABLE 1

| Compound # | n | R |
|---|---|---|
| 1 | 1 | 4-chlorophenyl |
| 2 | 2 | 2,4-dichlorophenyl |
| 3 | 1 | 3-nitrophenyl |
| 4 | 1 | 3,4-dichlorophenyl |
| 5 | 2 | 2-methylphenyl |
| 6 | 1 | 3-fluorophenyl |
| 7 | 1 | 2-furanyl |
| 8 | 1 | 2-thienyl |
| 9 | 1 | 3-methoxyphenyl |
| 10 | 1 | 4-methylphenyl |
| 11 | 2 | 4-methylphenyl |
| 12 | 2 | 2-furanyl |
| 13 | 1 | 3-trifluoromethylphenyl |
| 14 | 1 | 4-ethanonephenyl |
| 15 | 1 | 2,6-dichlorophenyl |
| 16 | 2 | 2,6-dichlorophenyl |
| 17 | 2 | phenyl |
| 18 | 2 | 4-chlorophenyl |
| 19 | 2 | 3,5-dichlorophenyl |
| 20 | 1 | 4-butoxyphenyl |
| 21 | 1 | 3,5-dichlorophenyl |
| 22 | 1 | 4-benzoic acid, ethyl ester |
| 23 | 2 | 3-chlorophenyl |
| 24 | 2 | 4-trifluoromethylphenyl |
| 25 | 1 | 4-trifluoromethylphenyl |

TABLE 1-continued

| Compound # | n | R |
|---|---|---|
| 26 | 1 | 3-benzoic acid, methyl ester |
| 27 | 2 | 3-bromophenyl |
| 28 | 1 | 4-ethoxyphenyl |

TABLE 2

| CMPD # | $R^1$ | $R^2$ | $R^3$ | $R^4$ | X | n | M.P. (° C.) |
|---|---|---|---|---|---|---|---|
| 29 | H | H | H | $CO_2CH_3$ | O | 0 | 85–89 |
| 30 | H | H | H | $CO_2CH_3$ | O | 2 | 126–129 |
| 31 | H | H | H | $CO_2CH_3$ | O | 1 | 118–119 |
| 32 | H | $CH_3$ | H | H | S | 0 | oil |
| 33 | H | $CH_3$ | H | H | S | 1 | 73–75 |
| 34 | H | H | H | H | S | 2 | 99–101 |
| 35 | H | H | H | Br | S | 0 | 82–83 |
| 36 | H | H | H | Br | S | 1 | 113–114 |
| 37 | H | $CH_3$ | H | H | S | 2 | 60–62 |
| 38 | H | H | H | Br | S | 2 | 118–119 |
| 39 | H | H | $CO_2CH_3$ | $CH_3$ | O | 0 | 87–88 |
| 40 | H | H | Br | H | S | 0 | 74–75 |
| 41 | H | H | Br | H | S | 1 | 169–173 |
| 42 | H | H | Br | H | S | 2 | 126–127 |
| 43 | H | H | $CO_2CH_3$ | $CH_3$ | O | 2 | 156–157 |
| 44 | H | H | $CO_2CH_3$ | $CH_3$ | O | 1 | 147–148 |
| 45 | H | H | $CH_3$ | $CO_2CH_3$ | S | 1 | 150–152 |
| 46 | H | H | $CH_3$ | $CO_2CH_3$ | S | 2 | 125–126 |
| 47 | H | H | H | $CH_3$ | S | 0 | 62–63 |
| 48 | H | H | H | $CH_3$ | S | 1 | 109–111 |
| 49 | H | H | H | $CH_3$ | S | 2 | 101–102 |
| 50 | $CH_3$ | H | H | H | S | 1 | 114–115 |
| 51 | $CH_3$ | H | H | H | S | 2 | 147–148 |
| 52 | $CH_3$ | H | H | H | S | 0 | 70–72 |
| 53 | H | H | H | $CO_2CH_2CH_3$ | S | 0 | 68–69 |
| 54 | H | H | H | $CO_2CH_2CH_3$ | S | 1 | 109–110 |
| 55 | H | H | H | $CO_2CH_2CH_3$ | S | 2 | 123–124 |

TABLE 2-continued structure: R¹-O-N=... with R²,R³,R⁴,X on thiophene ring, [O]ₙ on S

| CMPD # | R¹ | R² | R³ | R⁴ | X | n | M.P. (° C.) |
|---|---|---|---|---|---|---|---|
| 56 | H | H | H | CN | S | 0 | 136–137 |
| 57 | H | H | H | CN | S | 1 | 160–162 |
| 58 | H | H | H | CN | S | 2 | 153–155 |
| 59 | H | H | H | Cl | S | 0 | 74–77 |
| 60 | H | H | H | Cl | S | 1 | 102 |
| 61 | H | H | H | Cl | S | 2 | 113–114 |
| 62 | H | H | H | CHO | S | 0 | 48–49 |
| 63 | H | H | H | NO$_2$ | S | 0 | 162–163 |
| 64 | H | H | H | NO$_2$ | S | 1 | 186–188 |
| 65 | H | H | H | NO$_2$ | S | 2 | 160–161 |
| 66 | H | H | H | CH=NOCH$_3$ | S | 2 | 168–170 |
| 67 | H | H | H | C$_6$H$_5$ | S | 0 | 100–103 |
| 68 | H | H | H | C$_6$H$_5$ | S | 1 | 144–147 |
| 69 | H | H | H | C$_6$H$_5$ | S | 2 | 85–98 |
| 70 | H | H | NO$_2$ | C$_6$H$_5$ | S | 0 | 140–145 |
| 71 | H | H | CH$_3$ | Br | S | 0 | oil |
| 72 | H | H | CH$_3$ | Br | S | 1 | 100–104 |
| 73 | H | H | Br | CH$_3$ | S | 0 | 64–67 |
| 74 | H | H | COOH | CH$_3$ | O | 0 | 188–189 |
| 75 | H | H | CONHC$_6$H$_5$ | CH$_3$ | O | 0 | 176–178 |
| 76 | H | H | CONHC$_6$H$_5$ | CH$_3$ | O | 1 | 182–183 |
| 77 | H | H | CONHC$_6$H$_5$ | CH$_3$ | O | 2 | 193–194 |

TABLE 2A

| CMPD # | R¹ | R² | R³ | R⁴ | X | n | M.P. (° C.) |
|---|---|---|---|---|---|---|---|
| 78 | H | H | H | H | S | 2 | 102–104 |
| 79 | H | H | H | H | S | 1 | 106–107 |

TABLE 3

| CMPD # | R¹ | R" | X | Y | n | M.P. (° C.) |
|---|---|---|---|---|---|---|
| 80 | H | H | O | N | 2 | 255 |
| 81 | H | H | O | N | 1 | 190–191 |
| 82 | H | H | O | N | 0 | 143–144 |
| 83 | H | H | S | N | 2 | 226–227 |
| 84 | H | H | S | N | 0 | 150–151 |
| 85 | H | H | S | N | 1 | 192–195 |
| 86 | H | H | S | CH | 0 | 132–134 |
| 87 | H | H | S | CH | 1 | 140–142 |
| 88 | H | H | S | CH | 2 | 150–154 |
| 89 | H | CH$_3$ | O | N | 1 | 209–210 |
| 90 | H | CH$_3$ | O | N | 2 | 215–216 |
| 91 | H | H | S | C—OCH(CH$_3$)$_2$ | 1 | oil |

TABLE 4

| CMPD # | R¹ | R⁸ | R⁹ | R¹⁰ | n | M.P. (° C.) |
|---|---|---|---|---|---|---|
| 92 | H | H | F | H | 2 | 136–138 |
| 93 | H | H | F | H | 1 | 132–133 |
| 94 | H | F | F | H | 2 | 106–108 |
| 95 | H | F | F | H | 1 | 128–130 |
| 96 | H | F | F | H | 0 | 63–65 |
| 97 | H | CF$_3$ | H | CF$_3$ | 1 | 110–113 |
| 98 | H | CF$_3$ | H | CF$_3$ | 0 | 44–48 |
| 99 | H | CF$_3$ | H | CF$_3$ | 2 | 76–78 |
| 100 | H | F | H | F | 0 | 103–104 |
| 101 | H | F | H | F | 2 | 108–110 |
| 102 | H | F | H | F | 1 | 138–139 |
| 103 | H | CO$_2$CH(CH$_3$)$_2$ | Cl | H | 0 | oil |
| 104 | H | CO$_2$CH(CH$_3$)$_2$ | Cl | H | 1 | 127–129 |
| 105 | H | CO$_2$CH(CH$_3$)$_2$ | Cl | H | 2 | 82–83 |
| 106 | H | H | CH=NOCH$_3$ | H | 1 | 85–87 |
| 107 | H | H | CH=NOCH$_3$ | H | 2 | 104–106 |

EXAMPLES OF BIOLOGICAL ACTIVITY

Example 10

Wood Preservative Efficacy Against Bacteria and Yeasts

Compositions were prepared by dissolving the compounds shown in Table 1 in 50% ethanol and further diluting with sterile distilled water. These dilutions were pipetted into Petri dishes and mixed with warm tryptose agar to reach an active ingredient concentration of 10 and 100 ppm. After cooling, the medium was inoculated with the bacteria listed below. After sufficient growth of the untreated cultures, the compounds were evaluated using the following rating system:

0=growth equal to control

1=inhibition of growth by the compound

2=no growth under the influence of the compound.

The scores measured for wood preservation efficacy of the compounds of this invention are listed in Table 5. In this Table, the higher numbers are the most preferred species.

Causal agents: Bacteria/Yeasts
 *Debaryomyces hansenii* (yeast)
 *Pseudomonas alcaligenes* (gram neg)
 *Bacillus cereus mycoides* (gram pos)
 *Pseudomonas aeruginosa* (gram neg)
 *Flavobacterium sp.* (gram neg)
 *Streptomyces albus* (gram pos)
 *Enterobacter aerogenes* (gram neg)
 *Escherichia coli* (gram pos)

colony of the test fungus. The fungi employed are listed below. After incubation at 22° C. and 70% relative humidity during a period long enough to allow significant growth of untreated controls, the diameters of the fungus colonies were measured and scored using the following rating system:

0=free of fungal growth

1=25% of fungal growth compared to untreated

2=50% of fungal growth compared to untreated

3=75% of fungal growth compared to untreated

4=Growth equal to that of untreated

The scores measured for wood preservation efficacy of the compounds of this invention are listed in Tables 6a and 6b. In these Tables, the lower numbers are the most preferred species.

Causal agents: Fungi
 *Coriolus versicolor*
 *Coniophora puteana* (syn. *C. cerebella*)

TABLE 5

DETAILED SCORES OF THE BACTERICIDAL ACTIVITY OF THE TEST COMPOUNDS

| | P. alcal-genes | B. cereus mycoides | P. aeru-ginosa | D. han-senii | | Flavo-bacter | | S. albus | | E. aero-genes | | E. Coli | |
|---|---|---|---|---|---|---|---|---|---|---|---|---|---|
| Conc. (ppm) | 100 | 100 | 10 | 100 | 100 | 10 | 100 | 10 | 100 | 10 | 100 | 10 | 100 | 10 |
| Aq. Dist. | 0 | 0 | 0 | 0 | 0 | 0 | 0 | — | 0 | — | 0 | — | 0 | — |
| EtOH | 0 | 0 | 0 | 0 | 0 | 0 | 0 | — | 0 | — | 0 | — | 0 | — |
| CMPD # | | | | | | | | | | | | | | |
| 1 | 1 | 2 | 2 | 0 | 2 | 2 | 2 | — | 2 | — | 0 | — | 2 | — |
| 2 | 0 | 2 | 0 | 0 | 2 | 2 | 2 | — | 0 | — | 0 | — | 0 | — |
| 3 | 2 | 2 | 2 | 1 | 2 | 1 | 2 | — | 2 | — | 1 | — | 2 | — |
| 4 | 1 | 2 | 2 | 0 | 2 | 2 | 2 | — | 2 | — | 0 | — | 2 | — |
| 5 | 0 | 2 | 0 | 0 | 2 | 0 | 2 | — | 2 | — | 0 | — | 1 | — |
| 6 | 1 | 2 | 0 | 0 | 2 | 2 | 2 | — | 2 | — | 0 | — | 2 | — |
| 7 | 1 | 2 | 0 | 0 | 2 | 0 | 2 | — | 0 | — | 0 | — | 0 | — |
| 8 | 2 | 2 | 0 | 1 | 2 | 2 | 2 | — | 2 | — | 2 | — | 2 | — |
| 9 | 0 | 0 | 0 | 0 | 0 | 0 | 0 | — | 0 | — | 0 | — | 0 | — |
| 10 | 1 | 2 | 0 | 1 | 2 | 2 | 2 | — | 2 | — | 0 | — | 2 | — |
| 11 | 1 | 1 | 0 | 1 | 2 | 0 | 2 | — | 1 | — | 0 | — | 0 | — |
| 12 | 0 | 0 | 0 | 0 | 0 | 0 | 0 | — | 0 | — | 0 | — | 0 | — |
| 13 | 0 | 2 | 2 | 0 | 2 | 2 | 2 | — | 2 | — | 0 | — | 2 | — |
| 14 | 1 | 2 | 2 | 1 | 2 | 0 | 2 | — | 2 | — | 0 | — | 2 | — |
| 15 | 0 | 1 | 0 | 0 | 1 | 0 | 0 | — | 0 | — | 0 | — | 0 | — |
| 16 | 0 | 2 | 0 | 0 | 2 | 0 | 0 | — | 0 | — | 0 | — | 0 | — |
| 17 | 0 | 0 | 0 | 0 | — | — | 0 | 0 | 0 | 0 | 0 | 0 | 0 | 0 |
| 18 | 1 | 2 | 0 | 0 | — | — | 2 | 0 | 2 | 0 | 0 | 0 | 0 | 0 |
| 19 | 0 | 2 | 0 | 0 | — | — | 2 | 0 | 2 | 0 | 0 | 0 | 0 | 0 |
| 20 | 0 | 0 | 0 | 0 | — | — | 0 | 0 | 0 | 0 | 0 | 0 | 0 | 0 |
| 21 | 2 | 2 | 2 | 0 | — | — | 2 | 2 | 2 | 2 | 0 | 0 | 0 | 0 |
| 22 | 1 | 2 | 2 | 0 | — | — | 2 | 1 | 2 | 1 | 0 | 0 | 0 | 0 |
| 23 | 0 | 0 | 0 | 0 | — | — | 0 | 0 | 0 | 0 | 0 | 0 | 0 | 0 |
| 24 | 0 | 2 | 2 | 0 | — | — | 2 | 0 | 2 | 1 | 2 | 0 | 0 | 0 |
| 25 | 1 | 2 | 2 | 0 | — | — | 2 | 1 | 2 | 2 | 0 | 0 | 0 | 0 |
| 26 | 0 | 2 | 2 | 0 | — | — | 2 | 0 | 2 | 0 | 0 | 0 | 0 | 0 |
| 27 | 1 | 2 | 2 | 0 | — | — | 2 | 2 | 2 | 2 | 0 | 0 | 2 | 1 |
| 28 | 0 | 2 | 1 | 0 | — | — | 2 | 0 | 2 | 1 | 0 | 0 | 0 | 0 |

Notes for Table 5 Ratings:
0 = growth equal to control
1 = inhibition of growth by the compound
2 = no growth under influence of the compound

Example 11

Wood Preservative Efficacy Against Fungi

The compounds shown in Table 1 were dissolved in 50% ethanol and then diluted with sterile water to give the required concentrations of 1 and 10 ppm in the test agar plates. Malt extract sugar (3%) was added aseptically and uniform distribution was obtained by shaking. Each plate was inoculated with a spore suspension or with a small piece of agar (1 mm) from the margin of an actively growing

*Chaetomium globosum*
*Aureobasidium pullulans*
*Penicillium islandicum*
*Cladosporium resinae* (syn *Hormonocanis resinae*, *Amorphotheca resinae*)
*Aspergillus niger*
*Aspergillus flavus*
*Trichoderma viride*
*Mucor sp.*

TABLE 6A

DETAILED SCORES OF FUNGICIDAL ACTIVITY OF TEST COMPOUNDS
(Test Dosage: 10 ppm)

| CMPD # | C. VERSICLOR | C. PUTEANA | C. GLOBOSUM | MUCOR SP | A. PULLULANS | P. ISLANDICUM | CL RESINAE | A. NIGER | A. FLAVUS | T. VIRIDE |
|---|---|---|---|---|---|---|---|---|---|---|
| CNTRL | 4 | 4 | 4 | 4 | 4 | 4 | 4 | 4 | 4 | 4 |
| 1 | 0 | 2 | 0 | — | 3 | 0 | 2 | 0 | 0 | 2 |
| 2 | 2 | 4 | 4 | — | 4 | 4 | 3 | 4 | 4 | 2 |
| 3 | 0 | 2 | 3 | — | 3 | 3 | 4 | 3 | 2 | 3 |
| 4 | 0 | 0 | 0 | — | 2 | 0 | 0 | 0 | 0 | 1 |
| 5 | 3 | 4 | 4 | — | 4 | 4 | 4 | 4 | 4 | 4 |
| 6 | 1 | 0 | 4 | — | 3 | 3 | 4 | 3 | 2 | 4 |
| 7 | 3 | 4 | 4 | — | 4 | 4 | 4 | 4 | 4 | 4 |
| 8 | 0 | 2 | 2 | — | 2 | 0 | 2 | 1 | 1 | 2 |
| 9 | 4 | 4 | 4 | 4 | 4 | 4 | 4 | 4 | 4 | 4 |
| 10 | 1 | 3 | 4 | 0 | 4 | 3 | 4 | 4 | 2 | 3 |
| 11 | 0 | 0 | 4 | 0 | 4 | 0 | 4 | 0 | 1 | 2 |
| 12 | 4 | 4 | 4 | 4 | 4 | 4 | 4 | 4 | 4 | 4 |
| 13 | 0 | 1 | 0 | 0 | 2 | 2 | 3 | 1 | 2 | 3 |
| 14 | 2 | 3 | 4 | 1 | 4 | 4 | 0 | 3 | 2 | 3 |
| 15 | 0 | 4 | 4 | 4 | 4 | 0 | 4 | 3 | 3 | 4 |
| 16 | 0 | 4 | 4 | 4 | 0 | 0 | 4 | 2 | 4 | 0 |

NOTES:
Rating Scale for Table 6A
0 = free of fungal growth
1 = 25% of growth compared to untreated control
2 = 50% of growth compared to untreated control
3 = 75% of growth compared to untreated control
4 = growth equal to that of untreated control

TABLE 6B

DETAILED SCORES OF THE FUNGICIDAL ACTIVITY OF THE TEST COMPOUNDS

| | G. VERSICLOR | | G. PUTEANA | | C. GLOBOSUM | MUCOR SP | | A. PULLULANS | P. ISLANDICUM | CL RESINAE | A. NIGER | A. FLAVUS | | T. VIRIDE |
|---|---|---|---|---|---|---|---|---|---|---|---|---|---|---|
| CONC (ppm) | 10 | 1 | 10 | 1 | 10 | 100 | 10 | 10 | 10 | 10 | 10 | 10 | 1 | 10 |
| Aq. Dist. | 4 | 4 | 4 | 4 | 4 | 4 | 4 | 4 | 4 | 4 | 4 | 4 | 4 | 4 |
| EtOH | 4 | 4 | 4 | 4 | 4 | 4 | 4 | 4 | 4 | 4 | 4 | 4 | 4 | 4 |
| CMPD # | | | | | | | | | | | | | | |
| 17 | 4 | | 4 | | 4 | 4 | | | | | | 4 | | |
| 18 | 0 | 1 | 0 | | 0 | 0 | | 4 | 0 | 1 | 0 | 0 | 3 | 2 |
| 19 | 0 | 2 | 3 | | 0 | 2 | | 3 | 0 | 0 | 0 | 0 | | 2 |
| 20 | 4 | | 4 | | 4 | 4 | | 4 | 4 | 4 | 4 | 4 | | 4 |
| 21 | 0 | 3 | 0 | | 2 | 0 | 1 | 2 | 0 | 0 | 0 | 0 | 3 | 4 |
| 22 | 2 | | 0 | 3 | 4 | 0 | | 4 | 2 | 4 | 3 | 2 | | 3 |
| 23 | 4 | | 4 | | 4 | 4 | | 4 | 4 | 4 | 4 | 4 | | 4 |
| 24 | 0 | | 3 | | 4 | 4 | | 4 | 0 | 0 | 0 | 0 | | 2 |
| 25 | 0 | 3 | 0 | 2 | 3 | 0 | 3 | 3 | 1 | 0 | 0 | 0 | | 2 |
| 26 | 4 | | 4 | | 4 | 2 | | 4 | 4 | 4 | 4 | 4 | | 3 |
| 27 | 0 | | 0 | 3 | 4 | 0 | | 4 | 4 | 0 | 3 | 3 | | 2 |
| 28 | 3 | | 0 | | 4 | 1 | | 4 | 4 | 4 | 4 | 3 | | 3 |

NOTES:
Rating Scale for Table 6B
0 = free of fungal growth
1 = 25% of growth compared to untreated control
2 = 50% of growth compared to untreated control
3 = 75% of growth compared to untreated control
4 = growth equal to that of untreated control

Example 12

Control of Molds and Blue Stain Fungi in Stick Test

The compounds shown in Table 1 were dissolved in 50% ethanol and a dilution series was made using the same solvent. In 25 ml of each dilution, one oven-dried beech stick (73×18×2 mm) was drenched until saturated. Test dosages were 50, 100, 250, 500, and 1000 ppm for blue stain fungi which were Aureobasidium pullulans and Sclerophoma pithyophila. Test dosages for the molds used (Trichoderma viride, Aspergillus niger) were 250, 500, 1000, 2500, and 5000 ppm.

After three hours the test solution was poured off and each stick was allowed to dry in a sterile laminar air flow. In each Petri dish one stick was placed on malt agar previously seeded with inoculum. Two drops of fungal or spore suspension were pipetted on the upper surface of the stick. The Petri dishes were then incubated at 22° C. and 90% relative humidity. The treated sticks were evaluated after sufficient growth of the fungus on the untreated control sticks. The following score system was used to rate the effectiveness of the compounds:

0=stick free of fungal growth

1=traces of fungal growth on stick

2=slight fungal growth (5 to 25% of the surface covered)

3=moderate fungal growth (25 to 50% of the surface covered)

4=vigorous fungal growth (greater than 50% of the surface covered).

For purposes of comparison of these compounds, these values were converted to threshold ranges. The threshold value in this system is defined as the minimum concentration of a particular compound which produces a score less than or equal to 1. These values are presented in Table 7.

TABLE 7

THRESHOLD VALUES (PPM) OF TEST COMPOUNDS IN STICK TEST FUNGI

| COMPOUND # | AUREOBASIDIUM PULLULANS | SCLEROPHOMA PYTHIOPHILA | ASPERGILLUS NIGER | TRICHODERMA VIRIDE |
|---|---|---|---|---|
| 1 | >1000 | 100–250 | 1000–2500 | 2500–5000 |
| 4 | 500–1000 | 50–100 | 250–500 | 500–1000 |
| 8 | 250–500 | 50–100 | 250–500 | 500–1000 |
| 11 | 1000 | <50 | 500–1000 | 2500–5000 |
| 13 | 500–1000 | 250–500 | 500–1000 | 1000–2500 |
| 16 | >1000 | 100–250 | >5000 | >5000 |
| 18 | 500–1000 | 100–250 | 250–500 | <250 |
| 19 | 250–500 | 250–500 | 250–500 | <250 |
| 21 | 250–500 | 50–100 | <250 | <250 |
| 24 | 500–1000 | 250–500 | 250–500 | 500–1000 |
| 25 | 250–500 | 50–100 | <250 | <250 |
| 27 | >1000 | 500–1000 | 500–1000 | <250 |

Example 13

Activity Against Wood-Rotting Fungi such as *Coriolus versicolor* and *Coniophora puteana*

Sapwood blocks (50×20×6 mm) of Scots pine (*Pinus sylvestris*) and beech (*Fagus sylvatica*) were oven-dried at 104° C. The blocks were cooled, weighed, and impregnated with the test compound, by a vacuum treatment. Each concentration of the test compounds was applied to 7 replicates. By reweighing after each treatment, the uptake of active ingredient was calculated. Badly treated wood was discarded. For fixation of the active compound, the treated blocks were kept in a closed container for two weeks. The container was opened and the wood was dried for two more weeks. The test blocks were sterilized by gamma-irradiation (1.2 Mrad). Each treated block was placed on a mesh in an inoculated Petri dishes of malt agar, with an untreated (control) block.

All the blocks were exposed to fungal attack for eight weeks at 22° C. and 70% relative humidity. At the end of the incubation period, the blocks were freed from adhering mycelium, oven dried at 104° C., allowed to cool, and weighed. The percentage weight loss of each block was calculated. Invalid results, due to waterlogging or insufficient moisture content, were not taken into account.

The average weight loss of the treated blocks compared to the control blocks appears in Table 8.

TABLE 8

AVERAGE WEIGHT LOSS OF BLOCKS TREATED WITH TEST COMPOUNDS

| | CORIOLUS | | | CONIOPHORA | | |
|---|---|---|---|---|---|---|
| | UPTAKE | % WEIGHT LOSS | | UPTAKE | % WEIGHT LOSS | |
| CMPD # | g.a.i./m3 | TREATED | CONTROL | g.a.i./m3 | TREATED | CONTROL |
| 4 | 477 | 35 | 32 | 568 | 0.3 | 17 |
| | 1205 | 35 | 41 | 1356 | 0.3 | 21 |
| 6 | 482 | 25 | 33 | 555 | 0.0 | 29 |
| | 1163 | 19 | 41 | 1373 | −0.1 | 20 |
| 8 | 494 | 24 | 34 | 536 | 0.9 | 25 |
| | 1184 | 3.5 | 26 | 1346 | 0.7 | 31 |
| 11 | 485 | 5.4 | 29 | 530 | ND | ND |
| | 1162 | 8.3 | 30 | 1346 | 1.8 | 28 |
| 13 | 492 | 27 | 31 | 530 | −0.2 | 34 |
| | 1202 | 9.0 | 31 | 1271 | 0.1 | 32 |
| 18 | 488 | 32 | 31 | 579 | 0.0 | 41 |
| | 1173 | 39 | 40 | 1534 | −0.3 | 35 |
| 19 | 472 | 35 | 29 | 573 | 0.9 | 42 |
| | 1222 | 87 | 35 | 1456 | −0.3 | 37 |
| 21 | 496 | 38 | 35 | 582 | −0.1 | 42 |
| | 1203 | 22 | 33 | 1456 | −0.5 | 35 |
| 24 | 450 | 39 | 37 | 545 | 17.3 | 30 |
| | 1136 | 35 | 39 | 1374 | 0.9 | 29 |
| 25 | 482 | 37 | 38 | 533 | −0.7 | 30 |
| | 1175 | 21 | 44 | 1358 | −0.8 | 33 |
| 27 | 479 | 32 | 31 | 526 | 0.7 | 36 |
| | 1203 | 36 | 37 | 1347 | −0.5 | 34 |

NOTES FOR TABLE 8
ND = NO DATA

Example 14

In Vitro Activity Against Molds and Blue-Stain Fungi

Representative compounds were dissolved (2000 ppm) in a 2:3 solution of acetone:ethanol. The effect of the representative compounds on the growth of certain molds and blue-strain fungi were determined using a poison plate assay according to the following procedure: The solutions of the representative compounds prepared above were further diluted with sterile water to desired concentrations and poured into Petri dishes. Malt extract agar medium was then added aseptically to the Petri dishes and to Petri dishes containing no compound (controls). The Petri dishes were then shaken to provide a uniform distribution of the agar medium. Each Petri dish containing compound and each control Petri dish, was then inoculated with a fungus and incubated for a period of time sufficient to permit complete growth of the fungus in the respective control Petri dish. The Petri dishes containing compound were then examined to determine the amount of inhibition of fungi for each concentration of compound tested. The lowest concentration of compound which resulted in complete inhibition of a particular fungus was determined and recorded in Tables 9A and 9B below as the mininum inhibitory concentration (MIC) values.

TABLE 9A

MIC (ppm) of Compounds against Fungi

| Compound # | 8 | 34 | 57 | 58 | 60 | 61 | 83 | 85 | 87 |
|---|---|---|---|---|---|---|---|---|---|
| A. amstelodami | 10 | 5 | 10 | 5 | 5 | 5 | >25 | 5 | 5 |
| A. niger | 25 | 5 | 10 | 5 | 5 | <1 | >25 | 5 | 2.5 |
| A. versicolor | 10 | 5 | 10 | 5 | 2.5 | 2.5 | 25 | 2.5 | 2.5 |
| A. pullulans | >25 | 25 | >25 | 25 | 25 | 10 | >25 | 25 | 10 |
| C. cladosporioides | >25 | 25 | 25 | 10 | 25 | 10 | >25 | 25 | 25 |
| C. pilifera | 5 | 2.5 | 10 | 5 | 5 | 2.5 | 10 | 2.5 | 2.5 |
| F. solani | 25 | 25 | 25 | 10 | 10 | 5 | >25 | 25 | 10 |
| G. candidum | >25 | 25 | 25 | 25 | 25 | 10 | >25 | 10 | 25 |
| P. purpurogenum | >25 | 10 | 10 | 10 | 25 | 5 | >25 | 10 | 2.5 |
| P. variotii | >25 | 25 | 25 | 25 | 10 | 5 | >25 | 25 | 10 |
| P. violacea | 25 | 25 | 25 | 25 | 10 | 25 | >25 | 10 | 10 |
| S. atra | 10 | 5 | 10 | 5 | 5 | 2.5 | 5 | 2.5 | 2.5 |
| S. entoxylina | 10 | 5 | 10 | 5 | 5 | 10 | 10 | 5 | 5 |
| T. viride | >25 | >25 | >25 | 25 | 25 | 10 | >25 | 25 | 10 |
| U. atrum | 25 | 25 | 25 | 10 | 10 | 10 | >25 | 10 | 10 |

TABLE 9B

MIC (ppm) of Compounds against Fungi

| Compound # | A | 4 | 19 | 21 |
|---|---|---|---|---|
| A. amstelodami | 25 | 10 | 25 | 10 |
| A. niger | 5 | 2.5 | 2.5 | 5 |
| A. versicolor | 10 | 5 | 25 | 2.5 |
| A. ullulans | 10 | 10 | 25 | 25 |
| C. cladosporioides | 25 | 10 | 25 | 25 |
| C. pilifera | 10 | 5 | 10 | 2.5 |
| F. solani | >25 | 10 | >25 | 10 |
| G. candidum | >25 | 25 | >25 | 25 |
| P. purpurogenum | 10 | 10 | 25 | 10 |
| P. variotii | 25 | 10 | 25 | 10 |
| P. violacea | >25 | 25 | >25 | 10 |
| S. atra | 10 | 2.5 | 25 | 2.5 |
| S. entoxylina | 25 | 10 | 25 | 10 |
| T. viride | 25 | 25 | 25 | 25 |
| U. atrium | >25 | 25 | >25 | 10 |

A - 3,4,dichlorophenyl-1,4,2-oxathiazone

Example 15

Activity Against Blue-Stain Fungi and Molds on a Stick Test on Vermiculite

Beech sticks (73×18×2 mm) Fagus sylvatica were painted, allowed to dry, and sterilized by γ-radiation (1.2 mRad). Sticks were treated by coating each stick with a film containing 0.15% or 0.3% of the tested compound in a water-based placebo paint.

The coated sticks prepared above were then dipped in a spore suspension of pure culture of each fungus. Seven sticks each were placed in autoclaved Petri dishes (200 mm in diameter, 30 mm in height) containing 300 ml of vermiculite and 120 ml of water, and incubated for 12 weeks. The surfaces of the sticks were then examined for the growth of fungus and were evaluated according to the following scoring system:

0: No growth

1: Trace of growth of up to 1% coverage of the test inoculated area

2: Growth covering between 1 and 10% of the inoculated test area

3: Growth covering between 10 and 30% of the inoculated test area

4. Growth covering between 30 and 70% of the inoculated test area

5. Growth covering more than 70t of the inoculated test area.

The scores of compounds tested are presented in Table 10.

TABLE 10

Surface Scores of Wooden Sticks Treated with Paint Formulation

| | Compounds/% a. i. | | | | | | | | | | | | | | |
|---|---|---|---|---|---|---|---|---|---|---|---|---|---|---|---|
| | 8 | | 34 | | 36 | | 37 | | 38 | | 41 | | 42 | | |
| Organisms | 0.15 | 0.3 | 0.15 | 0.3 | 0.15 | 0.3 | 0.15 | 0.3 | 0.15 | 0.3 | 0.15 | 0.3 | 0.15 | 0.3 | Control |
| A. versicolor | 0 | 0 | 0 | 0 | 0 | 0 | 2 | 1 | 1 | 0 | 0 | 0 | 2 | 1 | 5 |
| A. pullulans | 0 | 0 | 0 | 0 | 0 | 0 | 3 | 2 | 2 | 0 | 0 | 0 | 2 | 1 | 5 |
| C. cladosporioides | 0 | 0 | 0 | 0 | 0 | 0 | 3 | 0 | 2 | 0 | 0 | 0 | 2 | 1 | 5 |
| P. purpurogenum | 0 | 0 | 4 | 1 | 1 | 1 | 3 | 1 | 3 | 3 | 2 | 1 | 4 | 2 | 5 |
| P. violacea | 4 | 0 | 4 | 1 | 3 | 1 | 5 | 4 | 4 | 4 | 4 | 3 | 4 | 3 | 5 |
| R rubra (y) | 1 | 1 | 3 | 0 | 0 | 0 | 4 | 3 | 3 | 0 | 3 | 0 | 3 | 1 | 5 |

TABLE 10-continued

Surface Scores of Wooden Sticks
Treated with Paint Formulation

Compounds/% a. i.

| | 8 | | 34 | | 36 | | 37 | | 38 | | 41 | | 42 | | |
|---|---|---|---|---|---|---|---|---|---|---|---|---|---|---|---|
| Organisms | 0.15 | 0.3 | 0.15 | 0.3 | 0.15 | 0.3 | 0.15 | 0.3 | 0.15 | 0.3 | 0.15 | 0.3 | 0.15 | 0.3 | Control |
| *S. chartarum* | 0 | 0 | 1 | 0 | 0 | 0 | 1 | 0 | 5 | 2 | 4 | 0 | 3 | 2 | 5 |
| *U. atrum* | 1 | 1 | 3 | 1 | 3 | 1 | 4 | 3 | 4 | 3 | 3 | 1 | 5 | 3 | 5 | y = yeast
0 = No growth
1 = Trace of growth of up to 1% coverage of the test inoculated area.
2 = Growth more than 1% and up to 10% coverage of test inoculated area.
3 = Growth more than 10% and up to 30% coverage of test inoculated area.
4 = Growth more than 30% and up to 70% coverage of test inoculated area.
5 = Growth more than 70% coverage of test inoculated area.

Example 16

Activity Against Blue-Stain Fungi and Molds in a Stick Test

Representative compounds of this invention were dissolved in 50% ethanol. Each compound was then diluted serially using 50% ethanol. Four (4) oven-dried beech sticks (73×18×2 mm) were drenched until saturated in 25 ml of each dilution of each compound, to prepare the treated sticks. After three (3) hours, the solutions containing the test compounds were poured off and the treated sticks were allowed to dry in a sterile laminar air flow. Each treated stick was then placed in a Petri dish which had been previously seeded with inoculum. Two drops of a test fungal or spore suspension were pipetted onto the upper surface of each treated stick. The Petri dishes containing the treated sticks were incubated at 22° C. and 90% relative humidity. The treated sticks were evaluated after there was sufficient growth of fungus on control sticks (i.e., untreated sticks) incubated in the same manner. The following score system was used:
  0: Stick free of fungal/mold growth
  1: Traces of fungal growth on the stick
  2: Slight growth (5 to 25% of the surface covered with fungal growth)
  3: Moderate growth (25 to 50% covered with fungal growth)
  4. Vigorous to maximum fungal growth (more than 50% growth)

The threshold (minimum) concentration of each compound tested necessary to obtain a score of 1–2 or 0, for each fungus tested is presented in Table 11 below.

TABLE 11

Threshold Concentrations (ppm) against Blue-stain Fungi and Molds in a Stick Test Fungi/Mold

| | Aureobasidium | | Sclerophoma | | *A. niger* | | Trichoderma | |
|---|---|---|---|---|---|---|---|---|
| CMPD # | score 1–2 | score 0 | score 1–2 | score 0 | score 1–2 | score 0 | score 1–2 | score 0 |
| 8 | 250–500 | >1000 | 50–100 | 100 | 250–500 | 1000 | 500–1000 | 1000 |
| 34 | 250–500 | >1000 | <50 | 100 | <250 | 500 | 500–1000 | 2500 |
| 50 | 100–500 | >1000 | 50–100 | 100 | 250–500 | 1000 | 1000–2500 | 5000 |
| 51 | 250–500 | >1000 | 50–100 | 100 | 250–500 | 500 | 500–1000 | 1000 |
| 54 | 250–500 | 500 | <50 | 100 | <250 | 500 | 500–1000 | 5000 |
| 57 | 250–500 | >1000 | <50 | 100 | <250 | 500 | 500–1000 | 1000 |
| 58 | 500–1000 | >1000 | <50 | 100 | <250 | 500 | 1000–2500 | 5000 |
| 60 | 100–250 | 1000 | <50 | 100 | <250 | 500 | 500–1000 | 2500 |
| 61 | 250–500 | >1000 | <50 | 100 | <250 | <250 | 1000–2500 | 2500 |
| 81 | 250–500 | >1000 | <50 | 250 | 250–500 | 500 | 500–1000 | 2500 |
| 85 | 250–500 | 1000 | <50 | 100 | <250 | 1000 | 1000–2500 | 2500 |
| 87 | 100–250 | 1000 | 50–100 | 100 | 250–500 | 1000 | 1000–2500 | 5000 |
| 89 | 100–250 | >1000 | <50 | 250 | 250–500 | 500 | 1000–2500 | 2500 |

0: Stick free of fungal growth
1: Traces of fungal growth on the stick
2: Slight growth (5 to 25% of the surface covered with fungal growth)

Example 17

Activity Against Blue-Stain Fungi and Molds in a Mold Cabinet Test

Using the methods described in BS3900: Part G6: 1989, British Standard Methods of test for paints, "Assessment of resistance to fungal growth", representative compounds of this invention were tested for activity against blue-stain fungus and molds in a mold cabinet test.

In brief, sticks of Scots pine (Pinus sylvestris) measuring 75×100×10 mm, were painted, allowed to dry, and sterilized by T-radiation (1.2 mRad).

Solutions of the tested compounds (0.15% and 0.3%) in water-based placebo paint were prepared. The sticks were then with each solution. The inoculation consisted of dipping the sticks in a mixed spore suspension, then placing them in a mold chamber and incubating them for 12 weeks. The surfaces were evaluated according the following score system:

0: No growth
1: Trace of growth of up to 1% coverage of the inoculated test area
2: Growth covering between 1 and 10% of the inoculated test area
3: Growth covering between 10 and 30% of the inoculated test area
4. Growth covering between 30 and 70% of the inoculated test area
5. Growth covering more than 70% of the inoculated test area.

The scores of compounds tested are presented in Table 12.

TABLE 12

Surface Scores in a Paint Formulation in a Mold Cabinet Test

| Compound # | Concentration (%) | Surface Score 6 weeks | Surface Score 12 weeks |
|---|---|---|---|
| 8 | 0.15 | 0 | 2.0 |
|   | 0.3 | 0 | 1.5 |
| 34 | 0.15 | 0.5 | 1.5 |
|   | 0.3 | 0 | 1.0 |
| 36 | 0.15 | 2.5 | 4.5 |
|   | 0.3 | 2.5 | 4.0 |
| 37 | 0.15 | 4.0 | 5.0 |
|   | 0.3 | 0 | 0 |
| 38 | 0.15 | 2.5 | 4.5 |
|   | 0.3 | 2.5 | 4.0 |
| 41 | 0.15 | 0 | 2.0 |
|   | 0.3 | 0.5 | 3.0 |
| 42 | 0.15 | 1.5 | 3.5 |
|   | 0.3 | 0.5 | 3.0 |
| Placebo | — | 5.0 | 5.0 |

0 = No growth
1 = Trace of growth of up to 1% coverage of the test inoculated area.
2 = Growth more than 1% and up to 10% coverage of test inoculated area.
3 = Growth more than 10% and up to 30% coverage of test inoculated area.
4 = Growth more than 30% and up to 70% coverage of test inoculated area.
5 = Growth more than 70% coverage of test inoculated area.

Example 18

Control of Molds and Sapstain Fungi in Mini-Board Test

Representative compounds of this invention to be tested, were suspended in an aqueous solution containing 7.5% GENAPOL X 080™ (Hoechst-Celanese Corporation), and 20% propylene glycol monomethyl ether, to prepare the test solutions. The concentration of the test compound in the test solution was 5000 ppm.

Deep frozen boards (300×50×10 mm) of freshly felled sapwood of Pinus sylvestrus (mini-boards) were thawed at room temperature. One half of each mini-board was immersed in a test solution for 20 seconds. The mini-boards were then sprayed with mixed spore suspension containing the following fungi:

*Aureobasidium pullulans,*
*Aspergillus amstelodami,*
*Ceratocystis pilifera,*
Cladosporium sp.,
Penicillium sp.,
*Sclerophomas entoxylina,* and
*Trichoderma viride,* and stored in incubation boxes at 25° C. and at 100% relative humidity, for three weeks. For each compound tested, each concentration of test solution was applied to five different mini-boards.

The efficacy of the test compounds was determined by comparing the fungal growth on both the treated and untreated parts of the mini-boards.

The degree of infection was scored according to the following scale:
0=Free of fungal growth
1=Traces of fungal growth
2=Little fungal growth
3=Moderate fungal growth
4=Vigorous to maximum growth (all surfaces covered with fungal growth)

The results of the mini-board evaluation are presented in Table 13 below.

TABLE 13

Surface Scores of Treated Mini-Boards

| CMPD # | 3 Week Incubation 1500 ppm | 3 Week Incubation 2500 ppm | 6 Week Incubation 1500 ppm | 6 Week Incubation 2500 ppm |
|---|---|---|---|---|
| 8 | 0 | 0 | 0.8 | 0.4 |
| 34 | 0 | 0 | 2.4 | 2.4 |
| 36 | 0.2 | 0 | 2.6 | 1.4 |
| 37 | 0 | 0 | 0.8 | 0.4 |
| 38 | 0.6 | 0.4 | 2.0 | 2.8 |
| 41 | 0.6 | 0.2 | 2.4 | 1.6 |
| 42 | 0 | 0 | 2.0 | 2.6 |
| 48 | 0 | 0 | 1.4 | 0.8 |
| 49 | 0 | 0 | 1.8 | 1.2 |
| 78 | 0.2 | 0.2 | 1.2 | 1.8 |
| 79 | 1.0 | 0 | 3.0 | 1.8 |

0 = Free of fungal growth
1 = Traces of fungal growth
2 = Little fungal growth
3 = Moderate fungal growth
4 = Vigorous to maximum growth (all surfaces covered with fungal growth)

What is claimed is:
1. A method for preserving wood or a composite wood material which comprises treating the wood or the composite wood material with a fungicidally or bactericidally effective amount of a compound of the formula

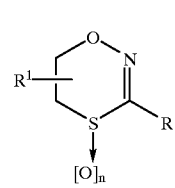

(II)

wherein n is 0, 1 or 2; $R^1$ is hydrogen, $C_1$–$C_4$ linear or branched alkyl, or benzyl: and R is 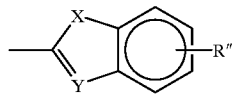
wherein X is oxygen or sulfur; Y is nitrogen, —CH—, or —C(C$_1$–C$_4$ alkoxy)—; and R" is hydrogen or C$_1$–C$_4$ alky.
* * * * *